United States Patent [19]

Sauter et al.

[11] Patent Number: 5,071,431
[45] Date of Patent: Dec. 10, 1991

[54] SUTURE RINGS FOR HEART VALVES AND METHOD OF SECURING SUTURE RINGS TO HEART VALVES

[75] Inventors: Joseph A. Sauter; Jeffrey L. Poehlmann; Louis A. Campbell, all of Austin, Tex.

[73] Assignee: Carbomedics, Inc., Austin, Tex.

[21] Appl. No.: 610,084

[22] Filed: Nov. 7, 1990

[51] Int. Cl.$^5$ .............................................. A61F 2/00
[52] U.S. Cl. ......................................... 623/2; 623/900
[58] Field of Search .................................... 623/2, 900

[56] References Cited

U.S. PATENT DOCUMENTS

| | | | |
|---|---|---|---|
| 3,491,376 | 1/1970 | Shiley | 623/2 |
| 3,824,629 | 7/1974 | Shiley | 623/2 |
| 4,363,142 | 12/1982 | Meyer | 623/2 |
| 4,535,483 | 8/1985 | Klawitter et al. | 623/2 |
| 4,743,253 | 5/1988 | Magladry | 623/2 |
| 4,863,460 | 9/1989 | Magladry | 623/2 |

Primary Examiner—Stephen C. Pellegrino
Assistant Examiner—Gary Jackson
Attorney, Agent, or Firm—John R. Merkling

[57] ABSTRACT

A suture ring for a mechanical heart valve comprised of essentially three parts: a stiffening ring which fits over an outer surface of the heart valve; a knit fabric sewing cuff attached to the stiffening ring, and a locking ring for securing the stiffening ring to the heart valve. The preferred embodiment comprises a locking ring which is generally crescent-shaped in cross-section and has a split ring configuration. Radial expansion or contraction is a first mode of deformation for the locking ring. The stiffening ring and the valve body can be locked together because the locking ring is capable of deforming in a second mode with respect to thickness of the ring. In the case of the preferred embodiment, the locking ring deforms by a slight flattening of the cresent cross-section of the ring.

55 Claims, 4 Drawing Sheets

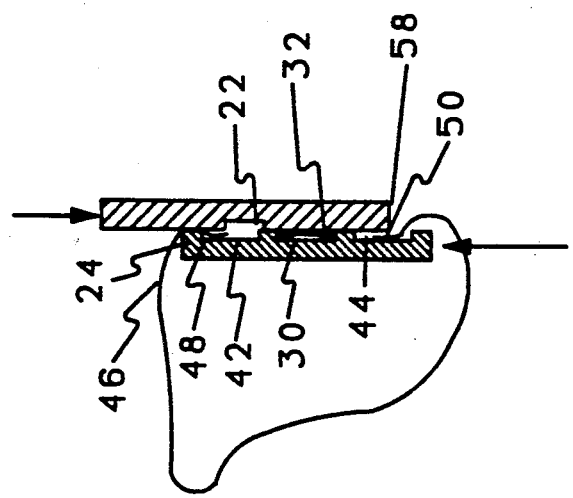
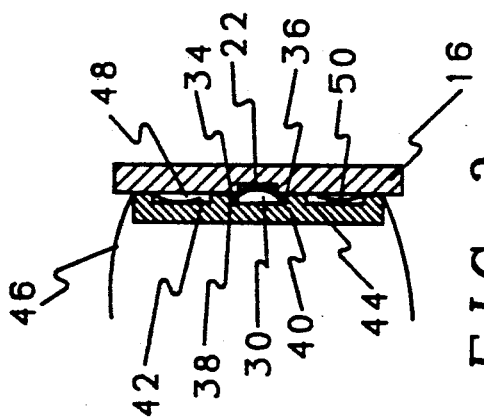
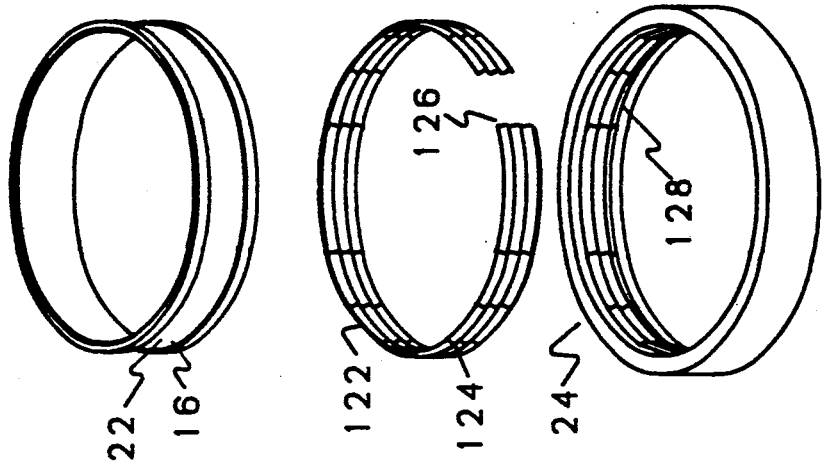
FIG. 3 FIG. 4 FIG. 11

SUTURE RINGS FOR HEART VALVES AND METHOD OF SECURING SUTURE RINGS TO HEART VALVES

BACKGROUND OF THE INVENTION

Our invention is directed to an improved suture ring for a prosthetic heart valve and to a method and apparatus for securing the suture ring to the heart valve.

Mechanical artificial heart valves for humans are frequently fabricated from carbon and coated with another form of carbon known commercially as Pyrolite TM, a trademark of Carbomedics, Inc., the assignee of our present invention. Pyrolitic carbon is employed because of its unusual nonthrombogenic properties. Human blood does not readily coagulate on contact with it. Moreover, it is lightweight, hard and quite strong.

A standard implantable mechanical heart valve usually has an annular valve housing or body to provide a passageway for blood. Occluders are mounted in the annular body and open or close the blood flow passageway. Usually there are one or two occluders, but occasionally triple occluder configurations have been proposed. On the outside of the valve body there is usually an external, circumferential surface configured as a groove. The purpose of this groove is to facilitate attachment of a suture ring to the valve body.

The suture ring is used to sew the heart valve to the patient's heart tissue. The ring generally comprises a knit fabric tube which is rolled into a toroidal form and which is secured about the heart valve body in the circumferential groove. Various methods and apparatus have been proposed for securing the suture ring to the heart valve. It is known, for instance, to bind the ring into the groove with a plastic thread. It has also been proposed to form a rotatable suture on the heart valve using heat shrinkable plastic material, as disclosed in U.S. Pat. No. 3,781,969. U.S. Pat. No. 3,491,376 suggests that a suture ring should be formed as a separate sub-assembly which should then be attached to the heart valve. In the '376 patent, the suture ring is described as including a resilient annular member which is temporarily deformed, so as to snap onto the valve body. U.S. Pat. No. 3,579,642 proposes the use of metal snap rings which must be radially expanded to place the suture ring about the valve body. In such fabrication techniques, however, there is a risk of potential damage to the suture rings when the ring is mechanically expanded to place it about the valve body.

In U.S. Pat. No. 4,743,253, Magladry proposed a two-part suture ring comprising the knit fabric and an internal crescent-shaped ring which would be deformed inwardly by electromagnetic forming to clamp the heart valve while permitting relative rotation between the suture ring and the heart valve.

Despite these efforts, there remains a need for improved techniques for attaching the relatively flexible knit fabric of the suture ring to the rigid, sometimes brittle material of the mechanical heart valve and for reinforcing the heart valve.

SUMMARY OF OUR INVENTION

We have invented a suture ring comprised of essentially three parts: a stiffening ring which fits over an outer surface of a heart valve; a knit fabric sewing cuff attached to the stiffening ring, and a locking ring for securing the stiffening ring to the heart valve. We have designed and describe herein several alternative embodiments, but our preferred embodiment comprises a locking ring which is generally crescent-shaped in cross-section. The locking ring is a split ring configuration so that it can be easily placed within the stiffening ring without deforming the stiffening ring and without plastic deformation or damage to the locking ring. This radial expansion or contraction is a first mode of deformation for the locking ring. The stiffening ring and the valve body can be locked together because the locking ring is capable of deforming in a second mode. In the case of our preferred embodiment, the locking ring deforms by a slight flattening of the crescent cross-section of the ring. This second mode of deformation resists uncoupling of the stiffening ring and the heart valve. The suture rings described herein share the common characteristic that they have two modes of deformation: one mode for assembly of the locking ring and the heart valve and second mode for the assembly of the suture ring combination and the heart valve.

With the foregoing in mind, it is a object of our present invention to provide an improved suture ring for a heart valve and method for securing suture rings to heart valves.

Another object of our invention is to provide a suture ring comprising three elements: a sewing cuff, a stiffening ring and locking ring.

It is an object of our invention to provide locking ring in a suture ring and heart valve combination wherein the locking ring has two modes of deformation.

Another object of our invention is to provide such a locking ring wherein one mode of deformation is useful in assembling a suture ring combination and a second mode of locking ring deformation is useful in assembling the suture ring combination and the heart valve.

These and other objects and advantages of our invention will become apparent from the following detailed description taken with reference to the accompanying drawings.

BRIEF DESCRIPTION OF THE DRAWINGS

FIG. 3 is a cross-section of the three components of FIG. 2 taken along line 3—3 and showing the components an assembled configuration.

FIG. 4 is a cross-sectional view of the components of FIG. 2 taken along line 3—3, showing the components during assembly.

FIGS. 5-11 are alternative embodiments of our invention.

DETAILED DESCRIPTION OF OUR PREFERRED EMBODIMENTS

Figures 1, 2:
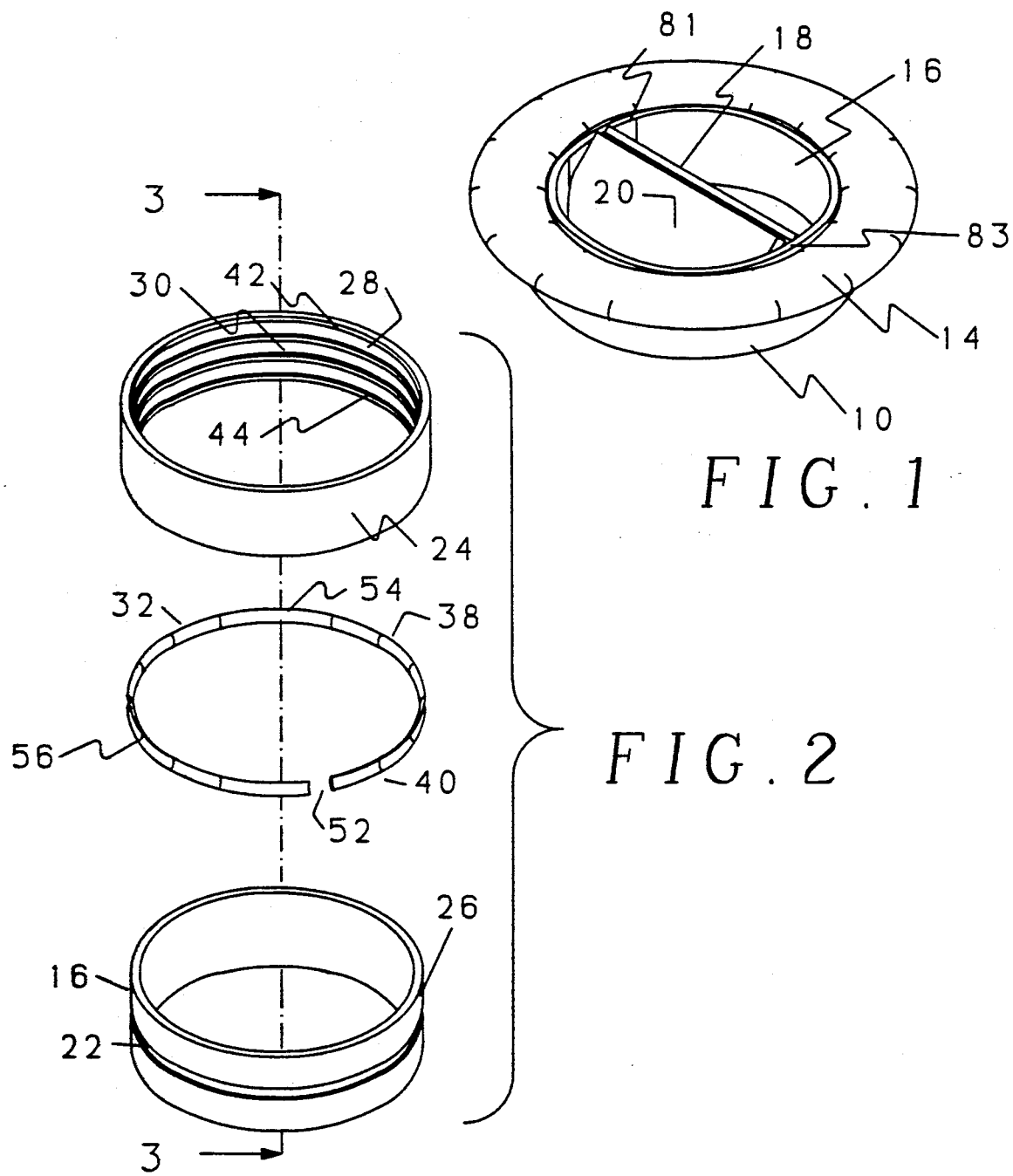
FIG. 1 is a perspective view of a prosthetic mechanical heart valve with a suture ring.
FIG. 2 is an exploded perspective view of a stiffening ring, locking ring and heart valve annulus according to our present invention.

We will now describe our preferred embodiments of our invention with reference to the accompanying drawings. In the drawings, like numerals will be used to designate like parts throughout.

FIG. 1 is a perspective view of a mechanical heart valve generally designated 10, with a suture ring 14 in accordance with our present invention. The heart valve 10 comprises a annular valve body 16 upon which the suture ring 14 is mounted. Within the annular valve body, leaflets 18 and 20 control the flow of blood through the valve. A bileaflet heart valve is illustrated, but our invention can easily be used with a monoleaflet or multileaflet valve.

Our preferred embodiment is illustrated in FIGS. 2, 3 and 4. As seen FIG. 2, the annular ring 16 of the heart valve 10 is provided with a circumferential exterior groove 22. The groove 22 is relatively narrow and shallow and is generally symmetrically spaced along the axial length of the annular valve body 16.

A stiffening ring fits snugly around an exterior surface 26 of the annular valve body. The stiffening ring is preferably comprised of a rigid, biocompatible material such as cobalt-chromium or Elgiloy. On an inner surface 28, three circumferential grooves are provided. A central groove 30 is placed so that it will be centered over the valve body groove 22 when the stiffening ring 24 and the valve body 16 are engaged. As can be seen in FIG. 3, the central groove 30 is slightly wider in an axial direction than the valve body groove 22. This enables the central groove 30 and the valve body groove 22 to cooperate with a locking ring 32 as will be described hereafter. We prefer that the central groove 30 have relatively steep side walls 34, 36 to engage upper and lower edges 38, 40 respectively, of the locking ring 32. The stiffening ring 24 further comprises an upper capture groove 42 above the central groove 30, and a lower capture groove 44 below it. A U-shaped Dacron sewing cuff 46 surrounds the annular valve body 16. The cuff 46 can be sewn onto cardiac tissue to affix the heart valve 10 within a human heart. When the annular valve body 16, the stiffening ring 24 and the locking ring 32 are assembled, edges of the sewing cuff 46 are caught between the locking ring 24 and the stiffening ring 24 whereby the annular valve body 16 is held in place. As seen in FIG. 3 an upper edge 48 is caught in the upper capture groove 42 and a lower edge 50 is caught in the lower capture groove 44. To enhance capture, the edges 48, 50 should be slightly thickened with respect to the overall thickness of the Dacron sewing cuff 46. Edge stitching is our presently preferred method of thickening. Other possibilities might include melting, or an adhesive bead glued along the edge or a ring attached to the edge.

As can be seen in FIG. 2, the locking ring 32 is split by a gap 52. The locking ring 32 comprises a metallic ring. We prefer to use 40% chrome elgiloy, a cobalt chrome alloy of available from the Elgiloy Co. The locking ring 32 comprises, in cross-section, a crescent-shaped ribbon having a convex inner surface 54 and a concave outer surface 56. It will be apparent that the orientation of the crescent can be reversed without departing from the teachings of our invention. The distance between the upper edge 38 and the lower edge 40 of the locking ring should be slightly less than the width of the central groove 30. To assemble the heart valve 10, the locking ring 32 is compressed circumferentially, closing the gap 52 or even causing the ends of the ring to overlap. This mode of deformation permits the ring to be placed into the central groove 30 of the stiffening ring 24. The edges 48, 50 of the sewing cuff 46 are placed in the capture grooves 42, 44 and the annular valve body 16, with leaflets in place, is slid into the stiffening ring, as shown in FIG. 4. As the annular valve body 16 is pressed into a stiffening ring 24, a lower edge 58 passes over the locking ring 32 deforming the locking ring in a second manner or mode, by flattening the locking ring slightly. As seen in FIG. 4, this presses the upper and lower edges 38, 40 of the locking ring away from each other and towards the upper and lower edges 34, 36 of the central groove 30. As the central groove 22 of the annular valve body 16 aligns with the central groove 30 of the stiffening ring, the locking ring 32 resumes its original shape and springs into the circumferential groove 22. The sewing cuff 46 is then locked onto the heart valve. There is, of course, the possibility of a slight axial movement between the annular valve body 16 and the stiffening ring 24, but this movement is negligible.

The forgoing represents the preferred embodiment of our invention, but other configurations of locking rings are possible. In each, two modes of deformation are provided: a first mode of deformation so that the circumference of the locking ring can be changed while the locking ring is being placed on the stiffening ring and a second mode of deformation so that the locking ring can be compressed into a groove, preferably in the stiffening ring, while the stiffening ring and the annular valve body are being assembled. For some of the embodiments, a frustro-conical installation tool, described below, must be used to place the annular valve body within the stiffening ring.

Figure 12:
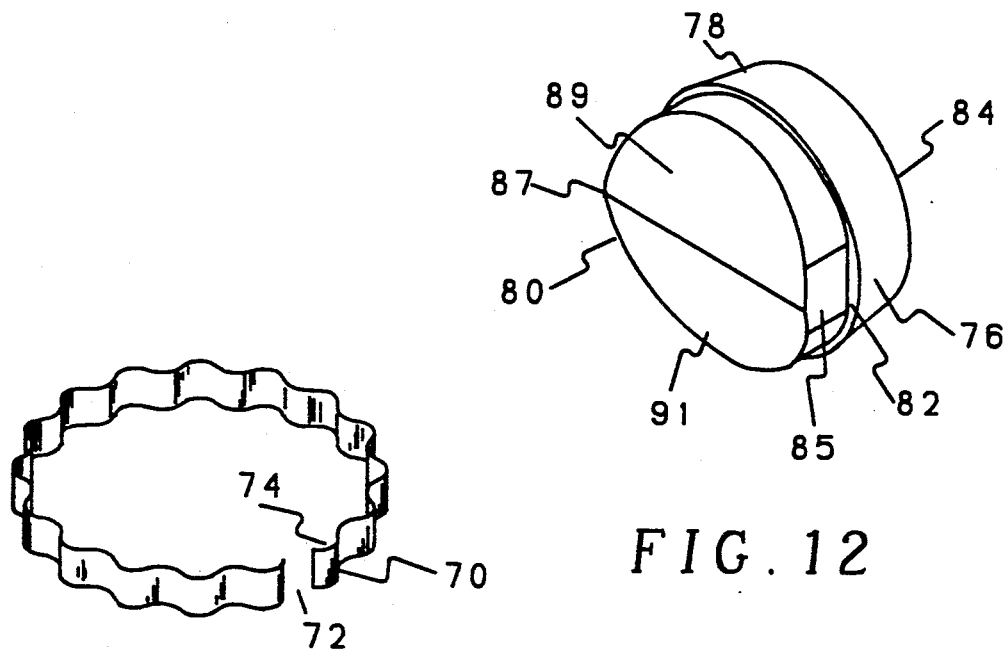
FIG. 12 is a perspective view of a tool for assembling the heart valve and suture ring.
Figure 5:
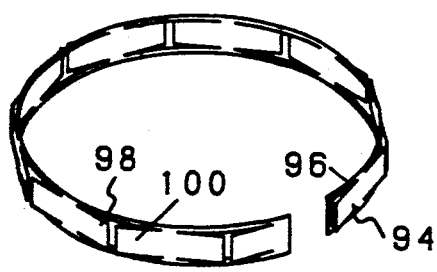

FIG. 5 shows a locking ring 70 which requires such an installation tool. The locking ring 70 comprises a split ring having a gap 72 for circumferential compression. The second mode of deformation is provided by radial sinusoidal waves 74. This second locking ring 70 can be placed in the stiffening ring 24 in the manner described above. However, to install the annular valve body 16, an installation tool 76 shown in FIG. 12 should be employed. The installation tool 76 comprises a frustro-conical segment 78 and a cylindrical segment 80 at a base 82 of the frustro-conical segment 78. A top 84 of the frustro-conical segment 78 should have a diameter which can fit within the locking ring 70. The base 82 should have a diameter equal to the outer diametric dimension of the annular valve body 16. The cylindrical portion 80 should be dimensioned to fit within the annular valve body 16. On the interior of many artificial heart valves, there are flattened areas 81, 83 (see FIG. 1) adjacent pivots on the leaflets. To accommodate this, flats 85, 87 should be provided on the cylindrical portion 80 of the installation tool 76. The cylindrical portion 80 has inclined bottom surfaces 89, 91 which fit against the leaflets and hold them in a closed position. To assemble a valve and suture ring, the locking ring 70 should be placed within the stiffening ring 24. The annular valve body 16 should be placed on the installation tool 76. The top 84 of the installation tool 76 should then be forced through the stiffening ring 24 and the locking ring 70. As the installation 76 tool passes through the stiffening ring the locking ring would be flattened into the central groove 30. As in the first embodiment, the second locking ring 70 is adapted to resume its shape when the circumferential groove 22 on the valve body 16 is adjacent the central groove 30.

Figure 6:
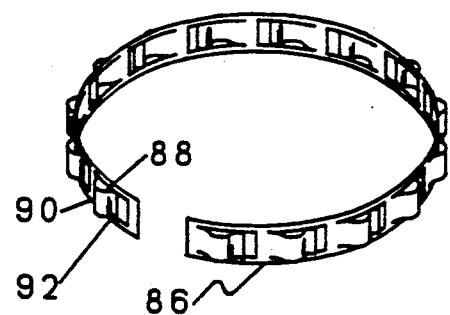

The embodiments of FIGS. 6, 7, 8 and 9 operate and are assembled in a manner similar to the second embodiment, illustrated in FIG. 5. FIG. 6 illustrates a third embodiment of a locking ring 86 having a plurality of circumferentially spaced wavy tabs 88. The tabs 88 are formed by making U-shaped cuts circumferentially around the locking ring 86 and then stamping the tabs to form a medial bend 90 and an end bend 92. The medial bend is curved in a radial direction with respect to the locking ring and the end bend is curved in the opposite direction.

Figure 7:
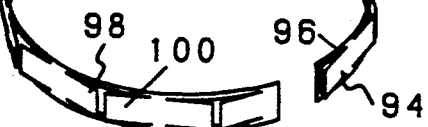

A fourth locking ring 94 is illustrated in FIG. 7. In the embodiment of FIG. 7, tabs are formed by making "H" shaped incisions through a strip 96. When the strip 96 is bent into a circular shape, opposed pairs of tabs 98, 100 are formed circumferentially around the locking ring 94.

Figure 8:
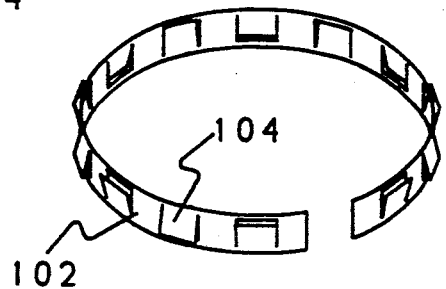

A fifth locking ring 102 is illustrated in FIG. 8. In this embodiment of our invention, radial tabs 104 are provided by making alternating U and n-shaped incisions along the metallic strip. The tabs 104 therefore, alternately open upwardly or downwardly. They can be bent radially outwardly, as shown, or radially inwardly.

Figure 9:
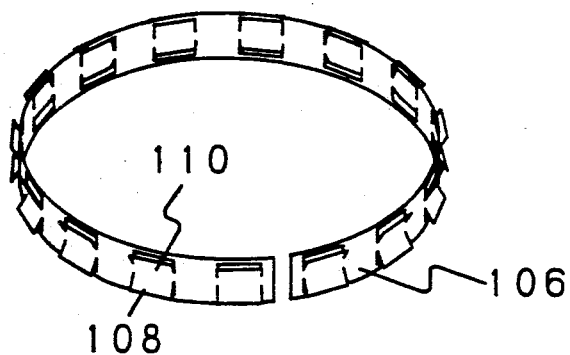

FIG. 9 illustrates a sixth locking ring 106. This locking ring 106 is similar to the locking ring 102 of FIG. 8. Pairs of tabs 108, 110 are formed by making an n-shaped incision over a U-shaped incision and by bending the resulting tabs, preferably in the same direction and outwardly as shown. This forms an upper circumferential row of tabs over a lower circumferential row of tabs.

Figure 10:
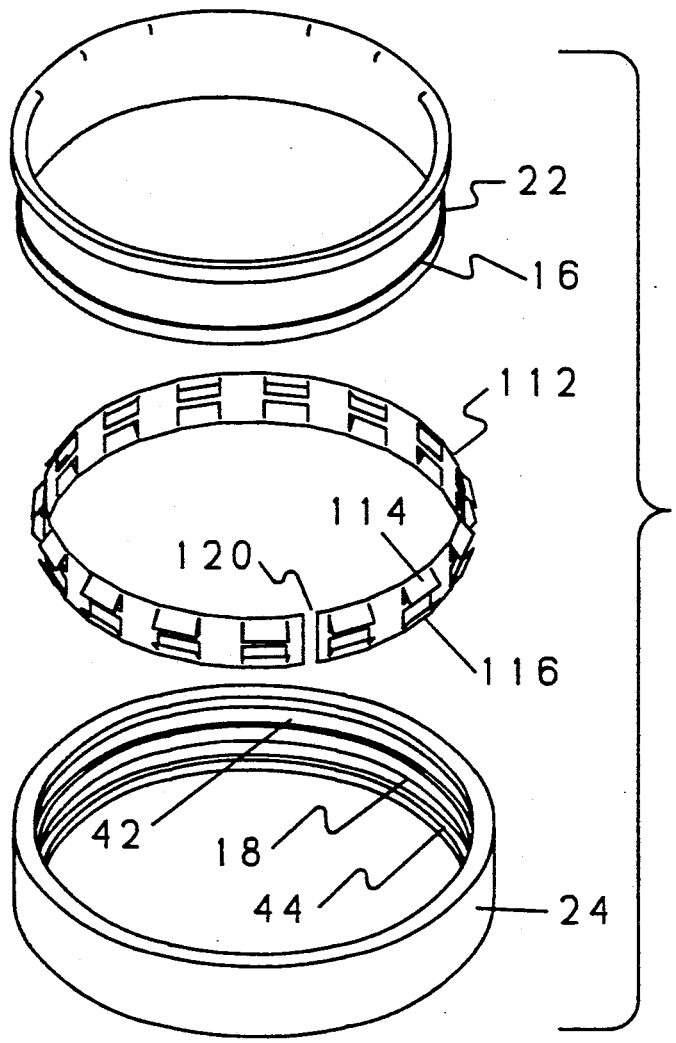

FIG. 10 illustrates a seventh variation, related to the sixth locking ring of FIG. 9. A seventh locking ring 112 has upper and lower tabs 114 and 116 as in the sixth locking ring 106. These tabs, however, are formed by making a U-shaped incision over an n-shaped incision. A central groove, such as central groove 30, is not provided on the stiffening ring 24. Instead, only an upper capture groove 42 and the lower capture groove 44 need be provided. These grooves form a central ridge 118 which is captured between the upper tabs 114 and the lower tabs 116 of the seventh locking ring 112. A much narrower slot 120 can be provided in the locking ring 112 because instead of being compressed circumferentially and placed on the stiffening ring, the seventh locking ring 112 is expanded circumferentially and placed first on the annular valve body 16. The circumferential groove 22 must, therefore, be wide enough to accommodate the width of the locking ring 112.

A technique similar to that used with the seventh locking ring is used in installation of the embodiment illustrated in FIG. 11. An eighth locking ring 122 shown in FIG. 11 comprises an elgiloy strip or ribbon with circumferential corrugations 124. As in the previous embodiments a slot 126 is provided for one mode of deformation. In cross-section, the corrugations 124 form essentially a sinusoidal or wavy shape in an axial direction. The locking ring 122 is expanded circumferentially and placed on the annular valve body 16. Once again, the circumferential groove 22 must be wide enough to accommodate this placement. Moreover, an additional width must be provided so that the corrugated stiffening ring 122 can be flattened. The stiffening ring 24 has interior circumferential corrugations 128 which correspond to the corrugations 124 of the stiffening ring 122. As the stiffening ring 128 is placed on the combination of the annular valve body 16 and the locking ring 122, the locking ring 122 would be flattened radially, in a second mode of deformation, but would resume its original shape to lock the annular valve body 16 and the stiffening ring 24 together.

Those skilled in the art will recognize that our invention may be embodied in other specific forms without departing from the spirit or essential characteristics thereof. The foregoing description is intended, therefore, to be in all respects illustrative and not restrictive, and the scope of our invention is defined by the following claims. All changes which become within the meaning of equivalency of the claims are intended to be embraced therein.

We claim as our invention:

1. An assembly comprising a mechanical heart valve and a suture ring,
   the heart valve having a generally cylindrical outer surface, and
   the suture ring comprising
      a stiffening ring having an inner surface adapted to fit adjacent said outer surface of said heart valve,
      a sewing cuff connected to said stiffening ring,
      means disposed between said cylindrical surface and said stiffening ring for locking said heart valve in said stiffening ring, said locking means having a circumferential dimension and a radial thickness and comprising means for changing said circumferential dimension and means for changing said radial thickness,
   means on said outer cylindrical surface of said heart valve for engaging said locking means and
   means on said inner surface of said stiffening ring for engaging said locking means,
   whereby said heart valve can be locked in said stiffening ring.

2. The assembly according to claim 1 wherein said engaging means on said outer cylindrical surface comprise a circumferential groove.

3. The assembly according to claim 1 wherein said engaging means on said inner surface of said stiffening ring comprise a circumferential groove.

4. The assembly according to claims 1, 2, or 3 wherein said locking means comprise a split ring.

5. The assembly according to claim 4 wherein said split ring comprises a crescent-shaped ribbon.

6. The assembly according to claim 5 wherein said sewing cuff comprises a ring of sewable material having a U-shaped radial cross section and an upper edge and a lower edge and wherein said stiffening ring further comprises an upper groove for capturing said upper edge of said sewing cuff and a lower groove for capturing said lower edge of said sewing cuff.

7. The assembly according to claim 4 wherein said split ring comprises a ribbon having a wavy shape in a radial direction with respect to said heart valve.

8. The assembly according to claim 7 wherein said sewing cuff comprises a ring of sewable material having a U-shaped radial cross section and an upper edge and a lower edge and wherein said stiffening ring further comprises an upper groove for capturing said upper edge of said sewing cuff and a lower groove for capturing said lower edge of said sewing cuff.

9. The assembly according to claim 4 wherein said split ring comprises a ribbon having a plurality of tabs circumferentially spaced along said ribbon.

10. The assembly according to claim 9 wherein said tabs each have a first end and a second free end and said tabs are affixed to said ribbon at said first ends and each tab comprises a medial bend having a curvature in a radial direction with respect to said split ring and an end bend having an opposite curvature.

11. The assembly according to claim 10 wherein said sewing cuff comprises a ring of sewable material having a U-shaped radial cross section and an upper edge and a lower edge and wherein said stiffening ring further comprises an upper groove for capturing said upper edge of said sewing cuff and a lower groove for capturing said lower edge of said sewing cuff.

12. The assembly according to claim 9 wherein the tabs each have a first end and a second end, said first and second ends being circumferentially spaced from each other, and the tabs are affixed to said ribbon at said first end thereof, said first end being oriented axially with respect to said ribbon, and said second end is displaced radially from said ribbon.

13. The assembly according to claim 12 wherein said sewing cuff comprises a ring of sewable material having a U-shaped radial cross section and an upper edge and a lower edge and wherein said stiffening ring further comprises an upper groove for capturing said upper edge of said sewing cuff and a lower groove for capturing said lower edge of said sewing cuff.

14. The assembly according to claim 12 wherein pairs of adjacent tabs have their respective first ends adjacent each other and their respective second ends remote from each other.

15. The assembly according to claim 14 wherein said sewing cuff comprises a ring of sewable material having a U-shaped radial cross section and an upper edge and a lower edge and wherein said stiffening ring further comprises an upper groove for capturing said upper edge of said sewing cuff and a lower groove for capturing said lower edge of said sewing cuff.

16. The assembly according to claim 9 wherein the tabs each have a first end and a second end, said first and second ends being axially spaced from each other, and the tabs are affixed to said ribbon at said first end thereof, said first end being oriented circumferentially with respect to said ribbon, and said second end is displaced radially from the ribbon.

17. The assembly according to claim 16 wherein said sewing cuff comprises a ring of sewable material having a U-shaped radial cross section and an upper edge and a lower edge and wherein said stiffening ring further comprises an upper groove for capturing said upper edge of said sewing cuff and a lower groove for capturing said lower edge of said sewing cuff.

18. The assembly according to claim 16 wherein said ribbon has an upper edge and a lower edge and wherein each pair of adjacent tabs has a first tab with a first end adjacent the upper edge and a second tab with its first edge adjacent the lower edge and the respective second ends of the first and second tabs are spaced radially from the ribbon.

19. The assembly according to claim 18 wherein said sewing cuff comprises a ring of sewable material having a U-shaped radial cross section and an upper edge and a lower edge and wherein said stiffening ring further comprises an upper groove for capturing said upper edge of said sewing cuff and a lower groove for capturing said lower edge of said sewing cuff.

20. The assembly according to claim 9 wherein said ribbon further comprises an upper and a lower circumferential row of tabs, each tab having first and second ends, said first and second ends being axially spaced from each other, and the tabs are affixed to said ribbon at said first end thereof, said first end being oriented circumferentially with respect to said ribbon, and said second end is displaced radially from said ribbon.

21. The assembly according to claim 20 wherein said sewing cuff comprises a ring of sewable material having a U-shaped radial cross section and an upper edge and a lower edge and wherein said stiffening ring further comprises an upper groove for capturing said upper edge of said sewing cuff and a lower groove for capturing said lower edge of said sewing cuff.

22. The assembly according to claim 20 wherein said ribbon has an upper edge and a lower edge and wherein each tab in said upper circumferential row is paired with an adjacent tab in said lower row.

23. The assembly according to claim 22 wherein the upper and lower tabs in each pair of tabs have their respective first ends adjacent each other.

24. The assembly according to claim 23 wherein said sewing cuff comprises a ring of sewable material having a U-shaped radial cross section and an upper edge and a lower edge and wherein said stiffening ring further comprises an upper groove for capturing said upper edge of said sewing cuff and a lower groove for capturing said lower edge of said sewing cuff.

25. The assembly according to claim 22 wherein the upper tab in each pair of tabs has its first end adjacent the upper edge of the ribbon and the lower tab in each pair of tabs has its first end adjacent the lower edge of the ribbon.

26. The assembly according to claim 25 wherein said sewing cuff comprises a ring of sewable material having a U-shaped radial cross section and an upper edge and a lower edge and wherein said stiffening ring further comprises an upper groove for capturing said upper edge of said sewing cuff and a lower groove for capturing said lower edge of said sewing cuff.

27. The assembly according to claim 4 wherein said split ring comprises a ribbon having a wavy axial cross section and wherein the stiffening ring has a mating wavy interior surface.

28. The assembly according to claim 27 wherein said sewing cuff comprises a ring of sewable material having a U-shaped radial cross section and an upper edge and a lower edge and wherein said stiffening ring further comprises an upper groove for capturing said upper edge of said sewing cuff and a lower groove for capturing said lower edge of said sewing cuff.

29. A suture ring for use with a mechanical heart valve, the suture ring comprising,
   a stiffening ring having an inner surface adapted to fit adjacent an outer surface of a heart valve,
   a sewing cuff connected to said stiffening ring,
   means adapted to be placed between said outer surface and said stiffening ring for locking said heart valve in said stiffening ring, said locking means having a circumferential dimension and a radial thickness and comprising means for changing said circumferential dimension and means for changing said radial thickness, and
   means on said inner surface of said stiffening ring for engaging said locking means.

30. The suture ring according to claim 29 wherein said engaging means on said inner surface of said stiffening ring comprise a circumferential groove.

31. The suture ring according to claims 29 or 30 wherein said locking means comprise a split ring.

32. The suture ring according to claim 31 wherein said split ring comprises a crescent-shaped ribbon.

33. The suture ring according to claim 32 wherein said sewing cuff comprises a ring of sewable material having a U-shaped radial cross section and and an upper edge and a lower edge and wherein said stiffening ring further comprises an upper groove for capturing said upper edge of said sewing cuff and a lower groove for capturing said lower edge of said sewing cuff.

34. The suture ring according to claim 31 wherein said split ring comprises a ribbon having a wavy shape in a radial direction with respect to said heart valve.

35. The suture ring according to claim 34 wherein said sewing cuff comprises a ring of sewable material having a U-shaped radial cross section and an upper edge and a lower edge and wherein said stiffening ring further comprises an upper groove for capturing said upper edge of said sewing cuff and a lower groove for capturing said lower edge of said sewing cuff.

36. The suture ring according to claim 31 wherein said split ring comprises a ribbon having a plurality of tabs circumferentially spaced along said ribbon.

37. The suture ring according to claim 36 wherein said tabs each have a first end and a second free end and said tabs are affixed to said ribbon at said first ends and each tab comprises a medial bend having a curvature in a radial direction with respect to said split ring and an end bend having an opposite curvature.

38. The suture ring according to claim 37 wherein said sewing cuff comprises a ring of sewable material having a U-shaped radial cross section and an upper edge and a lower edge and wherein said stiffening ring further comprises an upper groove for capturing said upper edge of said sewing cuff and a lower groove for capturing said lower edge of said sewing cuff.

39. The suture ring according to claim 36 wherein the tabs each have a first end and a second end, said first and second ends being circumferentially spaced from each other, and the tabs are affixed to said ribbon at said first end thereof, said first end being oriented axially with respect to said ribbon, and said second end is displaced radially from said ribbon.

40. The suture ring according to claim 39 wherein said sewing cuff comprises a ring of sewable material having a U-shaped radial cross section and an upper edge and a lower edge and wherein said stiffening ring further comprises an upper groove for capturing said upper edge of said sewing cuff and a lower groove for capturing said lower edge of said sewing cuff.

41. The suture ring according to claim 39 wherein pairs of adjacent tabs have their respective first ends adjacent each other and their respective second ends remote from each other.

42. The suture ring according to claim 41 wherein said sewing cuff comprises a ring of sewable material having a U-shaped radial cross section and an upper edge and a lower edge and wherein said stiffening ring further comprises an upper groove for capturing said upper edge of said sewing cuff and a lower groove for capturing said lower edge of said sewing cuff.

43. The suture ring according to claim 36 wherein the tabs each have a first end and a second end, said first and second ends being axially spaced from each other, and the tabs are affixed to said ribbon at said first end thereof, said first end being oriented circumferentially with respect to said ribbon, and said second end is displaced radially from the ribbon.

44. The suture ring according to claim 43 wherein said sewing cuff comprises a ring of sewable material having a U-shaped radial cross section and an upper edge and a lower edge and wherein said stiffening ring further comprises an upper groove for capturing said upper edge of said sewing cuff and a lower groove for capturing said lower edge of said sewing cuff.

45. The suture ring according to claim 43 wherein said ribbon has an upper edge and a lower edge and wherein each pair of adjacent tabs has a first tab with a first end adjacent the upper edge and a second tab with its first edge adjacent the lower edge and the respective second ends of the first and second tabs are spaced radially outward from the ribbon.

46. The suture ring according to claim 45 wherein said sewing cuff comprises a ring of sewable material having a U-shaped radial cross section and an upper edge and a lower edge and wherein said stiffening ring further comprises an upper groove for capturing said upper edge of said sewing cuff and a lower groove for capturing said lower edge of said sewing cuff.

47. The suture ring according to claim 36 wherein said ribbon further comprises an upper and a lower circumferential row of tabs, each tab having first and second ends, said first and second ends being axially spaced from each other, and the tabs are affixed to said ribbon at said first end thereof, said first end being oriented circumferentially with respect to said ribbon, and said second end is displaced radially from said ribbon.

48. The suture ring according to claim 47 wherein said sewing cuff comprises a ring of sewable material having a U-shaped radial cross section and an upper edge and a lower edge and wherein said stiffening ring further comprises an upper groove for capturing said upper edge of said sewing cuff and a lower groove for capturing said lower edge of said sewing cuff.

49. The suture ring according to claim 47 wherein said ribbon has an upper edge and a lower edge and wherein each tab in said upper circumferential row is paired with an adjacent tab in said lower row.

50. The suture ring according to claim 49 wherein the upper and lower tabs in each pair of tabs have their respective first ends adjacent each other.

51. The suture ring according to claim 50 wherein said sewing cuff comprises a ring of sewable material having a U-shaped radial cross section and an upper edge and a lower edge and wherein said stiffening ring further comprises an upper groove for capturing said upper edge of said sewing cuff and a lower groove for capturing said lower edge of said sewing cuff.

52. The suture ring according to claim 49 wherein the upper tab in each pair of tabs has its first end adjacent the upper edge of the ribbon and the lower tab in each pair of tabs has its first end adjacent the lower edge of the ribbon.

53. The suture ring according to claim 52 wherein said sewing cuff comprises a ring of sewable material having a U-shaped radial cross section and an upper edge and a lower edge and wherein said stiffening ring further comprises an upper groove for capturing said upper edge of said sewing cuff and a lower groove for capturing said lower edge of said sewing cuff.

54. The suture ring according to claim 31 wherein said split ring comprises a ribbon having a wavy axial cross section and wherein the stiffening ring has a mating wavy interior surface.

55. The suture ring according to claim 54 wherein said sewing cuff comprises a ring of sewable material having a U-shaped radial cross section and an upper edge and a lower edge and wherein said stiffening ring further comprises an upper groove for capturing said upper edge of said sewing cuff and a lower groove for capturing said lower edge of said sewing cuff.

* * * * *